United States Patent [19]

Kurz

[11] Patent Number: 4,614,497
[45] Date of Patent: Sep. 30, 1986

[54] ORTHODONTIC BRACKET FOR A DOUBLED-OVER TIE LIGATURE

[76] Inventor: Craven H. Kurz, 465 N. Roxbury Dr., #1011, Beverly Hills, Calif. 90210

[21] Appl. No.: 631,491

[22] Filed: Jul. 16, 1984

[51] Int. Cl.⁴ .............................................. A61C 3/00
[52] U.S. Cl. ......................................... 433/8; 433/10; 433/15
[58] Field of Search .................... 433/10, 15, 8, 18, 9, 433/11, 12, 13, 14, 16, 17

[56] References Cited

U.S. PATENT DOCUMENTS

| | | | |
|---|---|---|---|
| 1,584,501 | 5/1926 | Angle | 433/15 |
| 2,267,073 | 12/1941 | Boyd | 433/15 |
| 2,854,747 | 10/1958 | Lewis | 433/15 |
| 3,292,260 | 12/1966 | Jenkins | 433/15 |
| 3,421,221 | 1/1969 | Silverman et al. | 433/15 |
| 4,277,236 | 7/1981 | Kurz | 433/3 |

FOREIGN PATENT DOCUMENTS 974100 11/1964 United Kingdom ................ 433/15

Primary Examiner—John J. Wilson
Attorney, Agent, or Firm—Keith D. Beecher

[57] ABSTRACT

An orthodontic bracket having a transverse slot for receiving a conventional orthodontic arch wire, and which is constructed so that a resilient tie ligature used to retain the arch wire in place in the slot is supported on the bracket in a doubled-over configuration. This permits the arch wire to be more firmly and positively held in the transverse slot of the bracket, and it permits a reduction in size of the bracket because it eliminates the need for the gingival portion of the peripheral groove around the bracket which is used in the prior art brackets to retain the ligature.

9 Claims, 5 Drawing Figures

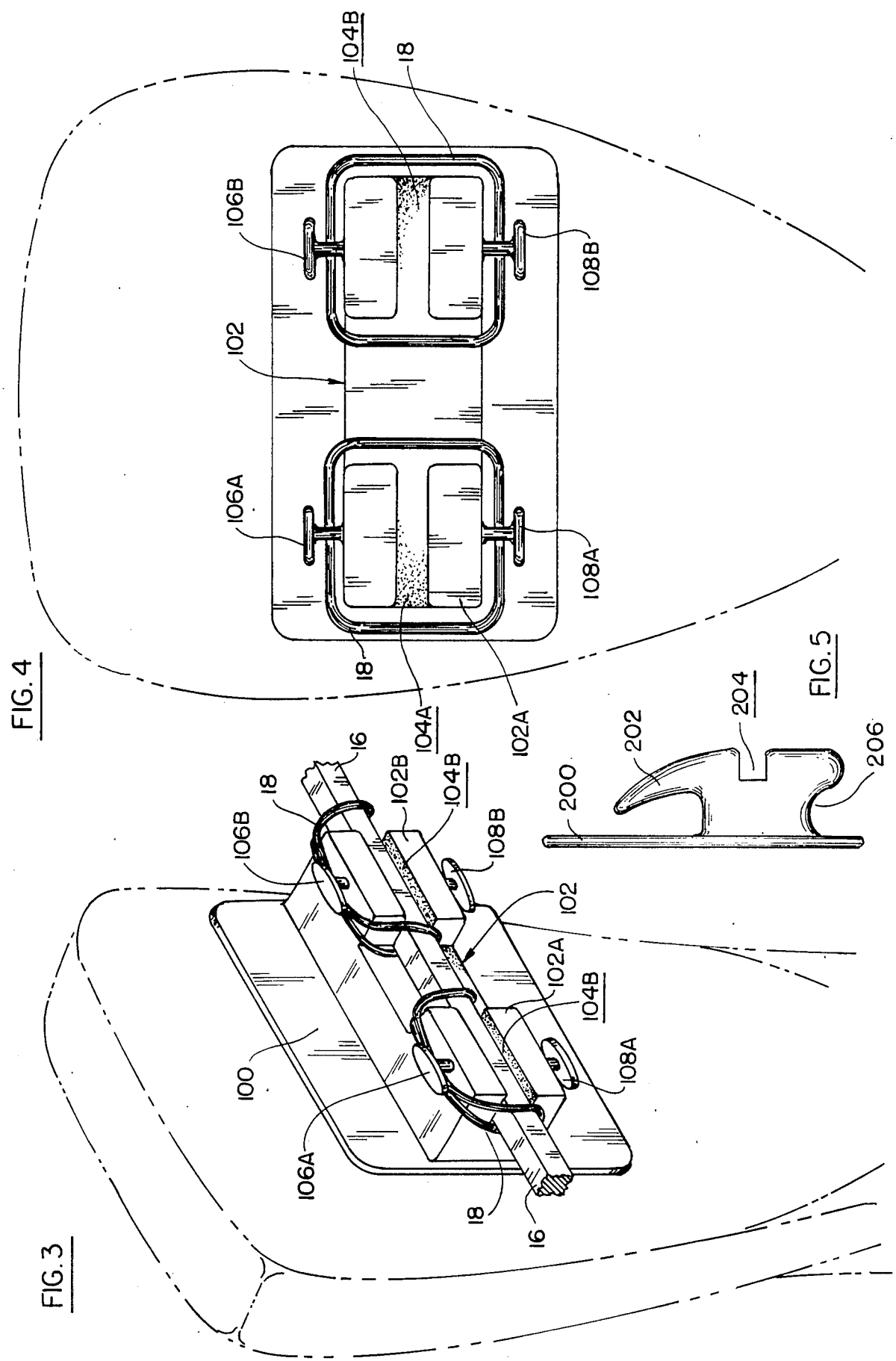

ORTHODONTIC BRACKET FOR A DOUBLED-OVER TIE LIGATURE

BACKGROUND OF THE INVENTION

It is usual for orthodontic brackets to be equipped with a transverse slot for receiving the arch wire, and with a peripheral groove for retaining the annular resilient tie ligature which serves to hold the arch wire in place in the transverse slot. In the usual prior art bracket, the ligature extends around the entire periphery of the bracket in a peripheral groove provided for that purpose. In accordance with the present invention, however, the tie ligature is supported entirely in the peripheral groove extending around the incisal portion of the bracket, so that the portion of the peripheral groove extending around the gingival portion of the bracket may be eliminated, and the incisal-gingival dimension of the bracket may be substantially reduced.

One of the embodiments of the invention to be described comprises a bracket equipped with lateral mesiodistal extending hooks at each end for temporarily retaining the ligature while the arch wire is being inserted into the transverse slot in the bracket, with the upper end of the ligature being supported in the peripheral groove extending around the incisal portion of the bracket. After the arch wire is in place, the lower end of the ligature is removed from the lateral hooks and doubled over the arch wire and inserted into the peripheral groove around the incisal portion of the bracket, so that both ends of the ligature are held in that groove. The lateral hooks may also be used to provide necessary anchorage for tooth rotation and translation thus enabling a reduction in the width of the bracket, in addition to the reduction in the height as described above.

The force exerted on the arch wire by the doubled-over configuration of the tie ligature in the appliance of the present invention provides a greater seating force on the arch wire into the transverse slot of the bracket as compared with the force exerted by the tie ligature extending around the periphery of the conventional bracket. This results in a greater control over the tooth by the arch wire which is firmly held in the depth of the transverse slot by the practice of the teaching of the present invention.

The resulting smaller bracket of the invention is aesthetically superior to the prior art brackets, and it is less likely to irritate the lips, cheeks, tongue or gingival tissue of the patient.

Because the gingival portion of the bracket of the invention can be reduced in dimension, the functional portion of the bracket may be placed closer to the gingival tissue, than is the case with the prior art brackets, reducing the likelihood of interference by the occlusion of the patient's teeth during mastication.

BRIEF DESCRIPTION OF THE DRAWINGS

FIG. 3 is a perspective view of a second embodiment of the invention which is suitable for mounting on the molars of the patient;

FIG. 4 is a front view of the embodiment of FIG. 3 prior to the insertion of the arch wire; and FIG. 5 is an end view of yet a further embodiment of the invention.

DETAILED DESCRIPTION OF THE ILLUSTRATED EMBODIMENTS

Figure 1:
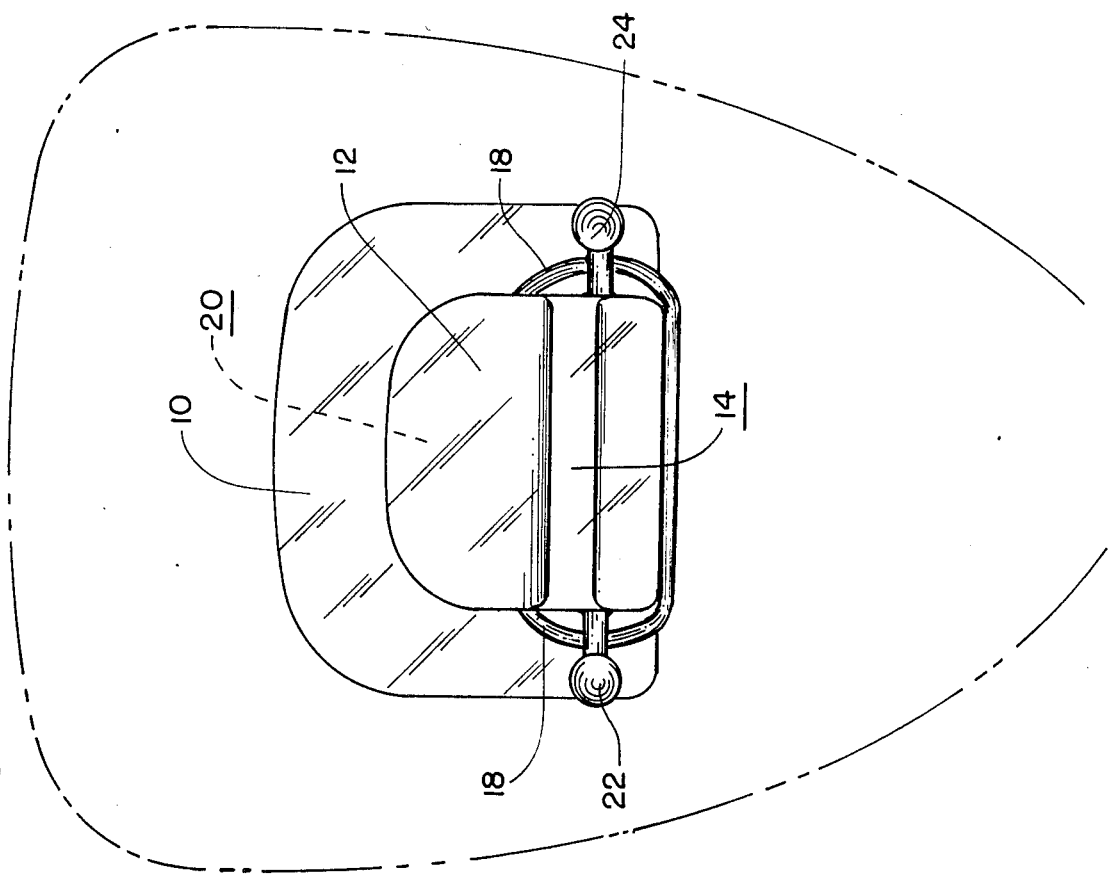
FIG. 1 is a perspective representation of a bracket constructed in accordance with one embodiment of the invention, and bonded in place on the tooth of a patient.
Figure 2:
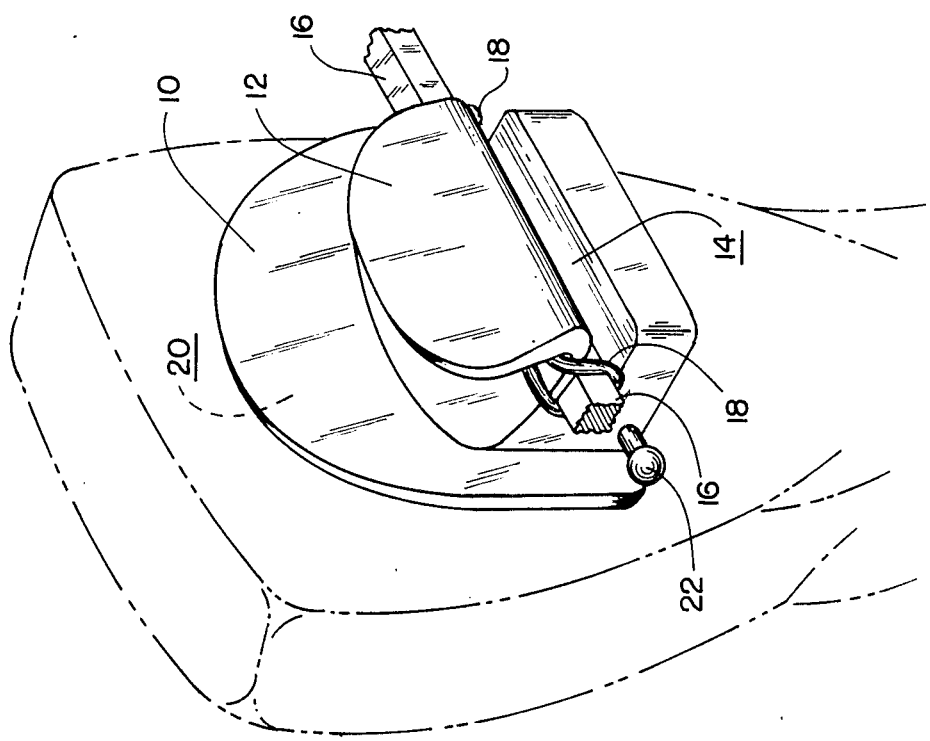
FIG. 2 is a front view of the bracket of FIG. 1 in place on the tooth of the patient, and prior to the insertion of the arch wire in the bracket, the bracket of FIGS. 1 and 2 being adaptable to be mounted on the incisors, canines and pre-molars of the patient.

The bracket of FIGS. 1 and 2 comprises a base 10 which is adapted to be bonded to the labial or lingual surfaces of the incisors, canines and pre-molars of the patient. a transverse slot 14. A usual arch wire 16 extends across the transverse slot, and is held in place by a doubled-over tie ligature 18. The tie ligature 18 is retained in a peripheral groove 20 which extends around the incisal portion of the bracket. The gingival portion of the bracket is foreshortened, as best shown in FIG. 2, since there is no need for the peripheral groove 20 to extend around the gingival portion of the bracket.

The bracket 12 is equipped with a pair of lateral hooks 22, 24 which extend outwardly from the ends of the bracket on the gingival portion thereof just below the transverse slot 14.

In order to retain the arch wire 16 in the transverse slot 14, the ligature tie 18 is looped around the peripheral groove 20 and around the hooks 22 and 24, as shown in FIG. 2. The arch wire is then placed across the bracket 12 within the transverse slot 14, and the ligature 18 is unhooked from the hooks 22, 24 and is looped over the arch wire 16 and is inserted into the peripheral groove 20 to assume the configuration shown in FIG. 1.

As stated above, the embodiment of the invention shown in FIGS. 3 and 4 is suitable to be mounted, for example, on the molars of the patient. The latter embodiment includes a base 100 which is adhesively bonded to the lingual or labial side of the tooth, and a bracket 102 attached to the base. Bracket 102, as shown, is in two sections 102A and 102B. These sections being spaced apart from one another in the mesial direction. Each of the brackets is provided with a transverse slot, the slots being designated 104A and 104B, and the arch wire 16 extends across the bracket and is retained in each slot by a doubled-over ligature 18.

In the embodiment of FIGS. 3 and 4, the ligatures 18 are retained by respective hooks 106A, 106B mounted on the sections 102A and 102B and extending in the incisal direction.

Additional hooks 108A and 108B are provided on the sections 102A and 102B to serve as temporary retainers for the ligatures as the arch wire 16 is being inserted into the transverse slots 104A and 104B.

As shown in FIG. 4, the ligatures 18 are first hooked around the hooks 106A, 108A and 106B, 108B, and the arch wire 16 is then inserted into the slots 104A and 104B. Then, each ligature 18 is unhooked from the corresponding hooks 108A and 108B, and is looped around the arch wire and hooked over the respective hooks 106A, 106B, as shown in FIG. 3.

In the embodiment of FIG. 5, a bracket 202 is mounted on a base 200, and has a transverse slot 204. In the bracket of FIG. 5, the temporary retainer means for the arch wire is provided by a shallow groove in the gingival side of the bracket. The ligature, as before, is removed from the latter groove, and doubled around the arch wire and hooked over the incisal end of the bracket after the arch wire is in place. This configuration of the double over type bracket would eliminate the need for lateral hooks and provide for a more narrow bracket mesiodistally for areas on the teeth that require small brackets both in the vertical and horizontal dimensions.

The invention provides, therefore, an improved orthodontic bracket which is constructed to permit the ligature tie to be doubled over the arch wire and to be completely retained at the incisal portion of the bracket, causing the arch wire to be firmly retained within the transverse slot in the bracket, and also permitting the bracket to be reduced in size.

It will be appreciated that while particular embodiments of the invention have been shown and described, modifications may be made. It is intended in the claims to cover all modifications which come within the true spirit and scope of the invention.

What is claimed is:

1. An orthodontic appliance comprising: a base adapted to be attached to a patient's tooth; an orthodontic bracket attached to said base having an incisal portion and a gingival portion foreshortened with respect to said incisal portion, and further having a transverse slot in the outer surface thereof extending thereacross transverse to and located between said incisal and gingival portions for receiving an arch wire; retrainer means mounted on the incisal portion of the bracket above said transverse slot; and an annular ligature having a first portion retained in said retainer means, and having a second portion looped around said arch wire at each end of said slot and doubled back and likewise retained by said retainer means.

2. The orthodontic appliance defined in claim 1, in which said annular ligature is resilient.

3. The orthodontic appliance defined in claim 1, in which said retainer means is formed by a groove in the bracket extending around the periphery of the incisal portion of the bracket.

4. The orthodontic appliance defined in claim 1, in which said retainer means comprises a hook mounted on the incisal portion of the bracket and extending outwardly from the bracket in the incisal direction.

5. The orthodontic appliance defined in claim 1, and which includes a hook mounted on the bracket on the gingival side of the transverse slot for temporarily retaining the ligature during insertion of the arch wire in the transverse slot.

6. The orthodontic appliance defined in claim 5, in which said hook extends in the mesial distal direction.

7. The orthodontic appliance defined in claim 5, in which said hook extends in the gingival direction.

8. The orthodontic appliance defined in claim 5, in which said hook comprises the side of a recess formed in the gingival portion of the bracket.

9. The orthodontic appliance defined in claim 1, and which includes a pair of mesial distal extending hooks mounted on opposite ends of the bracket on the gingival side of the transverse slot for temporarily retaining the ligature during insertion of the arch wire into the transverse slots.

* * * * *